US008962721B2

(12) United States Patent
Rao et al.

(10) Patent No.: US 8,962,721 B2
(45) Date of Patent: Feb. 24, 2015

(54) NUCLEATING AGENTS FOR POLYOLEFINS BASED ON ACETAL COMPOUNDS

(75) Inventors: Gandham Satya Srinivasa Rao, Maharashtra (IN); S. Muthukumaru Pillai, Maharashtra (IN); Virendra Kumar Gupta, Maharashtra (IN)

(73) Assignee: Reliance Industries Limited, Mumbai, Maharashtra (IN)

( * ) Notice: Subject to any disclaimer, the term of this patent is extended or adjusted under 35 U.S.C. 154(b) by 0 days.

(21) Appl. No.: 13/522,077

(22) PCT Filed: Jan. 14, 2011

(86) PCT No.: PCT/IN2011/000029
§ 371 (c)(1),
(2), (4) Date: Jul. 13, 2012

(87) PCT Pub. No.: WO2011/086583
PCT Pub. Date: Jul. 21, 2011

(65) Prior Publication Data
US 2013/0116366 A1 May 9, 2013

(30) Foreign Application Priority Data

Jan. 15, 2010 (IN) .................. 1894/MUM/2009

(51) Int. Cl.
C08K 5/06 (2006.01)
C08K 9/00 (2006.01)
C08G 8/04 (2006.01)
C07D 319/14 (2006.01)
C07D 319/08 (2006.01)
C08K 5/1575 (2006.01)
C07D 493/10 (2006.01)

(52) U.S. Cl.
CPC ............ C08K 5/1575 (2013.01); C07D 493/10 (2013.01)
USPC ........... 524/108; 106/505; 106/506; 549/335; 549/370; 549/374

(58) Field of Classification Search
CPC ..... C08K 5/1575; C08L 23/10; C07D 493/10
USPC ...................... 106/505, 506; 524/6, 108, 199; 549/335, 370, 374
See application file for complete search history.

(56) References Cited

U.S. PATENT DOCUMENTS

| 3,708,502 | A | * | 1/1973 | Wuskell et al. | ............... | 549/370 |
| 3,872,000 | A | * | 3/1975 | Hamada et al. | ............... | 210/732 |
| 6,323,298 | B1 | * | 11/2001 | Yanagihara et al. | .......... | 526/351 |
| 2002/0103302 | A1 | * | 8/2002 | Cecchin et al. | ............... | 525/247 |

FOREIGN PATENT DOCUMENTS

JP 7188246 A 7/1995

OTHER PUBLICATIONS

Chemical Research in Chinese University; Liang et al.; vol. 24, Issue 4, Jul. 2008, pp. 441-444.*
Machine translation, CN 101357925, Li et al.*
S.F. Marrian, "The Chemical Reactions of Pentaerythritol and Its Derivatives", Chemical Reviews, vol. 43, No. 1, Aug. 1948 (1948-08), pp. 149-202.
Ya Liang et al., "Chiral Seperation of Spiro-compounds and Determination Configuration", .Chemical Research in Chinese Universities, vol. 24, No. 4, Jul. 2008, pp. 441-444, abstract.
Rong-Bao Wei et al., "Synthesis of Sprio Third Generation Macromolecular Dendrimer", Chinese Journal of Organic Chemistry, No. 29, No. 2, 2009, pp. 274-278.
Al-Mughaid H et al., "Selective chemistry of tripentaerythritol—Synthesis of acetals and tehir derivative", Canadian Journal of Chemistry, NRC Research Press, CA, vol. 84, No. 4, Apr. 1, 2006, pp. 516-521.
Eliahu Bograchov, Journal of the American Chemical Society, vol. 72, No. 5, May 19, 1950, pp. 2268-2270.
Ernst D. Bergmann et al., Journal of the American Chemical Society, vol. 73, No. 4, Apr. 19, 1951, pp. 1774-1775.

* cited by examiner

Primary Examiner — Liam J Heincer
Assistant Examiner — Marilou Lacap
(74) Attorney, Agent, or Firm — Tim Tingkang Xia, Esq.; Morris, Manning & Martin, LLP

(57) ABSTRACT

Described herein are novel acetal compounds capable as nucleating agents for polyolefins. The present invention relates to such compounds synthesized by reacting aromatic aldehydes with polyols and further, to the achievement of high crystallization temperatures in polypropylene compositions upon dispersal therein of formulations containing one or more of the said acetal compounds.

5 Claims, No Drawings

NUCLEATING AGENTS FOR POLYOLEFINS BASED ON ACETAL COMPOUNDS

FIELD OF THE INVENTION

This invention relates generally to acetal compounds useful as nucleating agents for polyolefins and more particularly to novel acetal compounds obtained by reacting aromatic aldehydes with polyols and further, to improvements realized by use of one or more of said acetal compounds as nucleating agents for various polypropylene formulations.

BACKGROUND OF THE INVENTION

The term polyolefins here refers to mostly homo and random copolymers of polypropylene (PP). These polyolefins are used for various end use applications such as storage containers, medical devices, food packages, plastic tubes and pipes etc. In polyolefins, the uniformity in arrangement of crystals upon crystallization is a necessity to provide an effective, durable, and versatile polyolefin article. In order to achieve such desirable physical properties, it has been known that addition of certain compounds which provide nucleation sites for polyolefin crystal growth during moulding or fabrication. The polymers containing such nucleating compounds crystallize at a much faster rate than virgin polyolefin. Increase in crystallization temperature results in reduced cycle times. The nucleators provide nucleation sites for crystal growth during cooling of a polyolefin from molten state. The presence of nucleation sites can also provide clarification to the targeted polyolefin if the crystallites formed are uniform and smaller than the wave length of light. Thus, nucleating agents are very important to the polyolefin industry where obtaining faster, homogeneous crystallization and clarity are some of the critical requisites. Thermal stability, solubility among nucleation compositions, possession of surface topology capable of achieving nucleation, ability to induce nucleation with high clarity at low concentrations and avoidance of haze are few more of the desired properties of ideal nucleating agents and an object for achievement of such is truly a pressing need of art.

Study of the art reveals efforts towards attainment of the said properties. Inorganic compounds like pulverized clay, silicates, alkali salts, alkaline earth salts, aluminum salts, titanium salts, metal oxides and organic compounds including γ-quinacridone, 2-mercapiobenzimidazole, sorbitol/phosphate derivatives find mention in the art. However, these have not been able to satisfactorily and comprehensively address said problems of art.

Dibenzylidene sorbitol (DBS) derivatives are effective nucleating agents for polypropylene. They are prepared by the condensation of two moles of an aromatic aldehyde with one mole of carbohydrate like sorbitol, xylitol etc. Murai et al in U.S. Pat. No. 4,429,140, Machell in U.S. Pat. No. 4,562,265, and Kobayashi et al in U.S. Pat. No. 4,902,807 have disclosed suitable methods to prepare them. Hamada et al disclosed DBS as effective nucleating and clarifying agents for polyolefin in their U.S. Pat. No. 4,016,118. A large numbers of other acetals of sorbitol and xylitol including bis(p-methylbenzylidene) sorbitol (4-MDBS) were also disclosed. Mahaffey, Jr., in U.S. Pat. No. 4,371,645 disclosed di-acetals of sorbitol having at least one chlorine or bromine substituent in the aromatic ring. Polyolefin compositions based on sorbital derivatives as nucleating and clarifying agents for PP are disclosed in U.S. Pat. Nos. 6,582,503; 6,586,007 and 6,989,154. Currently Millard 3988 [1,3-O-2,4-bis(3,4-dimethylbenzylidene) sorbitol (3,4-DMDBS) produced by Milliken Chemical Company provide excellent clarification characteristics besides nucleation for various polyolefins.

Many others commonly known compounds are kaolin, talc etc which show high polyolefin crystallization temperatures but exhibit many drawbacks for industrial applications. For example, Camphanic acid exhibits high peak crystallization temperature in PP homopolymer formulations but exhibits very poor thermal stability and plate out during processing. Sometimes sodium benzoate, NA-11, exhibit deleterious nucleating efficiency when used in combination with calcium stearate. This is due to calcium ion from the stearate transfers position with the sodium ions of the nucleating agents, rendering the nucleating agents ineffective. Non-ionic acid neutralizers, such as dihydrotalcite (DHT4-A) used in conjunction with such nucleators reduce the above effects aesthetic characteristics, haze and higher costs. Other problems include dispersion, agglomeration of nucleating agent's leads to inconsistent nucleation, stiffness and impact variation in the polyolefin. DBS derivatives exhibit plate-out at high processing temperatures and if the aromatic rings are mono-substituted, show improved thermal stability but show organoleptic properties and as a result they cannot be used in medical devices and food packaging.

To address some of these problems there is still a need in the plastics industry to discover new compounds that do not exhibit some of the above problems and provide excellent peak crystallization temperatures with polyolefins.

OBJECTS OF THE INVENTION

It is an object of the present invention to synthesise new nucleating agents.

Another object of present invention is to use the synthesised novel acetal compounds as nucleating agents for polyolefins.

A further object of the invention is to provide compositions based on these nucleating compounds which exhibit high peak crystallization temperatures with polypropylene homo and polypropylene random copolymer.

SUMMARY OF THE INVENTION

Accordingly, this invention encompasses a nucleating agent, which induces a peak crystallization temperature (Tc) of at least 112° C., more preferably, 113° C. with a high Tc temperature of about 119° C. for random copolymer polypropylene formulation wherein the unnucleated polypropylene exhibits a melt flow of 12 g/10 min and peak crystallization temperature 109° C. measured by differential scanning calorimeter.

Additionally, this invention also encompasses a nucleating agent, which induces a standard peak crystallization temperature of at least 120° C. in a polypropylene homopolymer, wherein the unnucleated polypropylene random copolymer exhibits a melt flow of about 3 g/10 min and peak crystallization of 116° C.

DETAILED DESCRIPTION OF THE INVENTION

The novel acetal compounds are synthesised by the reaction of an aromatic aldehyde with or with out a carboxyl or alkyl group as substituent and a polyol. The polyols chosen are types of polyhydroxy alkanes typified by pentaerythritol, or their derivatives like dipentaerythritol etc. The product was purified, characterized and the structure was established. Various compositions were made by blending the synthesised novel acetal compounds separately with polyolefins. Various standard additives like antioxidants, acid scavengers, and dispersing agents were also added. All the compositions were compounded in a high speed branbery mixer and extruded in single screw extruder of Brabender Plasticorder. The synthesised acetal compounds provide excellent high peak crystallization temperatures in a variety of polyolefin formulations, particularly within polypropylene random copolymer and polypropylene homopolymer.

The inventive acetal nucleating agents are thus added to the polyolefin in an amount from about 50 ppm to about 10000 ppm by weight, most preferably from about 500 ppm to about 5000 ppm in order to provide the aforementioned beneficial characteristics.

The polyolefin polymers of the present invention may include aliphatic polyolefins and copolymers made from at least one aliphatic olefin and one or more co-monomers. Generally, the co-monomers, if present, will be provided in a minor amount, e.g., about 10 percent or less or even about 5 percent or less, based upon the weight of the polyolefin (e.g. Polypropylene random copolymer). Examples of olefin polymers whose nucleation can be improved conveniently according to the present invention are polymers and copolymers of aliphatic mono olefins containing 2 to about 6 carbon atoms which have an average molecular weight of from about 10,000 to about 2,000,000, preferably from about 30,000 to about 300,000, such as, without limitation, isotactic polypropylene, polypropylene random copolymer with ethylene, 1-hexene, 1-octene etc as comonomers.

It shall be evident to the person skilled in the art that all compounds and those obtained as products by mere permutation of reactants being aromatic aldehydes and polyols do not act as efficient nucleating agents. Also, a general trend in this regards cannot be drawn. Attention is requested to some embodiments and examples which elaborate on the unique features of the present invention. These examples are for mere illustration purposes only and do not restrict the ambit of the present invention.

PREFERRED EMBODIMENTS OF THE INVENTION

Examples based on the synthesis of nucleating agents and their compositions within the scope of the present invention are presented hereinafter. It will be amply evident to a person skilled in the art that these embodiments are for illustration purposes only and do not limit the scope of the present invention.

EXAMPLE 1

Synthesis of Acetal Compounds

Some pentaerythritol acetals synthesized and then tried as nucleating agents are shown below:

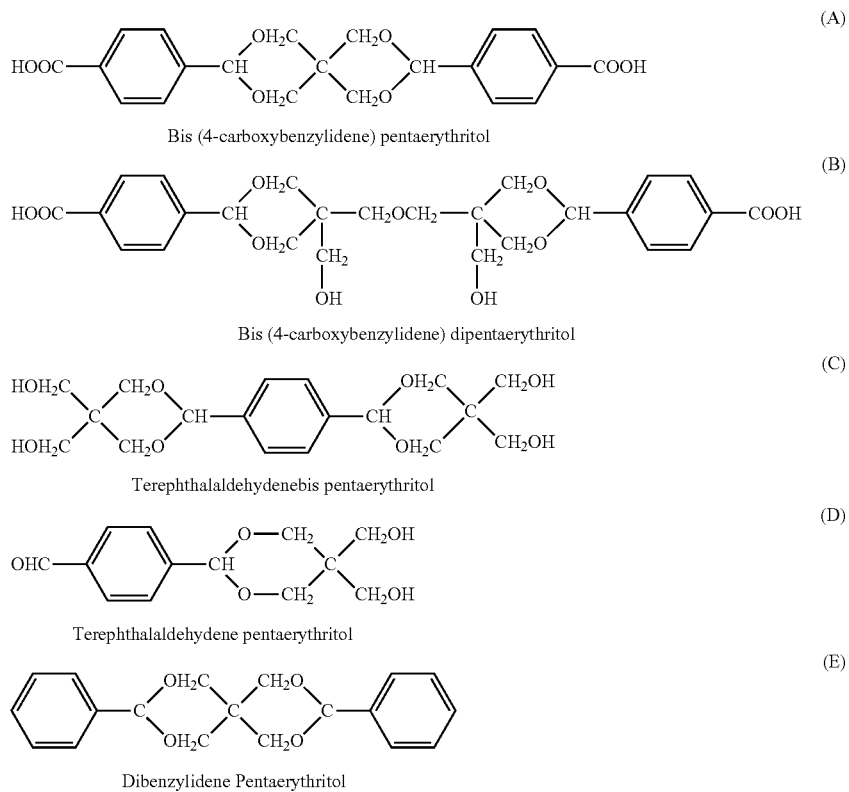

(A) Bis (4-carboxybenzylidene) pentaerythritol (B) Bis (4-carboxybenzylidene) dipentaerythritol (C) Terephthalaldehydenebis pentaerythritol (D) Terephthalaldehydene pentaerythritol (E) Dibenzylidene Pentaerythritol

EXAMPLE 2

Nucleation Reaction Standards

Polypropylene random copolymer (PRCP, unstabilized, 400 g, MI-12 from M/s Reliance Industries Limited, Hazira, Gujarat, India) was dry blended with 0.20 g of Irganox 1010, 0.32 g, 0.08 g Hydrotalcite DHT 4A, 0.16 g Glycerol Monostearate (Finstate 9500), 0.20 g calcium stearate and 0.80 g of nucleating agent in a high speed ribbon mixer at 80 RPM and extruded in single screw extruder of Brabender Plasticorder with a temperature profile of 170-200-230 225°

C. and 60 RPM. The extrudates were cooled, pelletized and dried for 2 hours at 80° C. and moulded. The synthesized acetal compounds were tested and compared with standard nucleating agents like Millard 3988, NA-21, Sodium Benzoate, and Potassium Benzoate. All the synthesised acetal compounds were tested as Nucleating agents. The typical compositions are given in Table 1.

EXAMPLE 3

Additional Standards for Nucleation

Vaseline oil (1 g) was taken in a ribbon mixer and heated to 120° C. under nitrogen. Irganox 1010 (0.5 g), Irganox 1076 (0.35 g), Irgafos PEPQ (0.15 g), Irgafos 168 (0.1 g) and 2.0 g of Dibenzylidene Pentaerythritol were added and heated for 5 min. To this mixture of additives, unstabilized polypropylene homopolymer (1000 g, Melt Index 3), calcium stearate (0.5 g) was added and mixed for 30 min for homogenization. The compounded material was extruded in single screw extruder of Brabender Plasticorder with a temperature profile of 170-200-230-225° C. and 60 RPM. The extrudates were cooled, palletized, dried and moulded.

EXAMPLE 4

Nucleation Efficiency Test

The Polyolefin compositions made in Examples 4 and 5 comprising the synthesised nucleating agents, Polypropylene random copolymer (PRCP), Polypropylene homopolymer (PP) and additives were subjected to nucleation efficiency test. The Peak Crystallization Temperatures (Tc) and Melting Temperatures (Tm) were measured on Differential Scanning calorimeter. The Tc was measured by heating the sample from 50° C. to 220° C. with a heating rate of 10° C./min and then held for 5 min at 220° C. and then again cooled the sample at the same rate until it reached the room temperature. The important crystallization temperatures were thus measured as the peak maxima during the individual crystallization exotherms for each sample. Polyolefins such as un-nucleated Polypropylene Random copolymer showed a crystallization temperature of about 109° C. where as with the addition of nucleating agents the Tc value increased to as high as 119° C. depending on the type of nucleating agent added. The super cooling $\Delta T(\Delta T=Tm-Tc)$ i.e. the difference between the melting temperature and crystallization temperature which is a function of overall rate of crystallization was measured. The smaller the difference between these temperatures, the greater is the rate of crystallization. The efficiency of various nucleating agents was evaluated by measuring the Tm, Tc and $\Delta T$ as given in Tables 2-3.

TABLE 1

Typical composition of Polypropylene with Nucleating Agents

| S. No. | Additives/polyolefins | Weight (g) | PPM |
|---|---|---|---|
| 1 | PP random copolymer (PRCP) | 400 | — |
| 2 | Irganox 1010 (From Ciba Geigy Ltd) | 0.20 | 500 |
| 3 | Ultranox 626, Bis (2,4-Di-Tert-butylphenyl) Pentaerythritol diphosphite (From Ciba Geigy Ltd) | 0.32 | 800 |
| 4 | Hydrotalcite DHT 4A (Kyowa Chemical Ind. Co Ltd) | 0.08 | 200 |
| 5 | Calcium Stearate | 0.20 | 500 |
| 6 | Finastate 9500 (Glycerol Monostearate) | 0.16 | 400 |
| 7 | Nucleating agent | 0.80 | 2000 |

TABLE 2

Nucleating efficiency of Acetal nucleating agents in Polypropylene

| S. No. | Compositions | Tm (° C.) | Tc (° C.) | Tm – Tc (° C.) |
|---|---|---|---|---|
| 1 | PP random copolymer (PRCP) | 149 | 109 | 40 |
| 2 | PRCP + Millard 3988 (standard 1) | 150 | 121 | 29 |
| 3 | PRCP + NA - 21 (standard 2) | 149 | 119 | 30 |
| 4 | PRCP + Dibenzylidene pentaerythritol | 150 | 111 | 39 |
| 5 | PRCP + Bis (4-Carboxybenzylidene) pentaerythritol (A) | 150 | 119 | 31 |
| 6 | PRCP + Bis (4-Carboxybenzylidene) di-pentaerythritol (B) | 149 | 116 | 33 |
| 7 | PRCP + Bis(4-Carboxybenzylidene) D-sorbitol | 150 | 116 | 34 |
| 8 | PRCP + Terephathaldehydene D-Sorbitol | 148 | 109 | 39 |
| 9 | PRCP + Terephathaldehydene di Pentaerythritol (C) | 150 | 115 | 35 |
| 10 | PRCP + Terephthaldehydene pentaerythritol (D) | 150 | 113 | 37 |
| 11 | PP homopolymer | 165 | 116 | 49 |
| 12 | PP + Dibenzylidene pentaerythritol (E) | 165 | 120 | 45 |

S. Nos. 2-10 contains PP random copolymer/nucleating agent/standard additives. 11-12 contains PP homopolymer/nucleating agent/standard additives.

Yet other advantages of the present invention will become apparent to those skilled in the art from the foregoing description and drawings wherein there is described and shown a preferred embodiment of the present invention. As will be realized, the present invention is capable of various other embodiments and that its several components and related details are capable of various alterations, all without departing from the basic concept of the present invention. Accordingly, the drawings and descriptions will be regarded as illustrative in nature and not as restrictive in any form whatsoever. Modifications and variations of the process and methods described herein will be obvious to those skilled in the art. Such modifications and variations are intended to come within the scope of the present invention.

The invention claimed is:

1. A composition useful for nucleation of polyolefin, comprising:
    an acetal compound, selected from the group consisting of Bis(4-carboxybenzylidene) pentaerythritol and Bis(4-carboxybenzylidene) dipentaerythritol;
    an antioxidant, selected from the group consisting of Pentaerythritol Tetrakis(3-(3,5-di-tert-butyl-4-hydroxyphenyl)propionate), Octadecyl 3-(3,5-di-tert-butyl-4-hydroxyphenyl)propionate, [4-[4-bis(2,4-ditert-butylphenoxy)phosphanylphenyl]phenyl]-bis(2,4-ditert-butylphenoxy)phosphane and Tris-(2,4-di-tert-butylphenyl)phopshite;
    an acid scavenger of calcium stearate; and
    a dispersing agent of petroleum paraffin oil for achievement of nucleation upon dispersal in polyolefin formulations.

2. An improved process for nucleation of polyolefins, said process comprising providing a polyolefin formulation and admixing therewith composition of claim 1, wherein process improvements characterized by substantial increase in peak crystallization temperatures, high clarity and absence of haze in the nucleation product are achieved using an effective concentration of said acetal compound, said effective concentration being in the range between 50 ppm to 10000 ppm by weight.

3. The improved process for nucleation of polyolefins according to claim 2, wherein the said polyolefin is selected from aliphatic polyolefins and copolymers comprising at least one each among aliphatic olefins and co-monomers.

4. The improved process for nucleation of polyolefins according to claim 2, wherein peak crystallization temperature achieved is at least 112° C. for random copolymer polypropylene formulation.

5. The improved process for nucleation of polyolefins according to claim 2, wherein peak crystallization temperature achieved is at least 120° C. for homopolymer polypropylene formulation.

* * * * *